(12) United States Patent
Linares

(10) Patent No.: US 8,784,451 B2
(45) Date of Patent: Jul. 22, 2014

(54) ELEVATING INSERT FOR CERVICAL SPINAL VERTEBRAE

(75) Inventor: Miguel A. Linares, Bloomfield Hills, MI (US)

(73) Assignee: Linares Medical Devices, LLC, Auburn Hills, MI (US)

(*) Notice: Subject to any disclaimer, the term of this patent is extended or adjusted under 35 U.S.C. 154(b) by 588 days.

(21) Appl. No.: 12/776,982

(22) Filed: May 10, 2010

(65) Prior Publication Data
US 2010/0312278 A1 Dec. 9, 2010

Related U.S. Application Data

(60) Provisional application No. 61/184,183, filed on Jun. 4, 2009.

(51) Int. Cl.
*A61B 17/70* (2006.01)

(52) U.S. Cl.
CPC .................. *A61B 17/7062* (2013.01)
USPC ....................................... 606/249

(58) Field of Classification Search
CPC ........... A61F 2002/30159; A61F 2002/30161; A61F 2002/30168; A61F 2002/30176; A61F 2002/30182; A61B 17/7068; A61B 17/7062
USPC ......................... 606/246–249, 263, 282, 293; 623/17.15–17.16
See application file for complete search history.

(56) References Cited

U.S. PATENT DOCUMENTS

| 5,607,425 | A | * | 3/1997 | Rogozinski | 606/264 |
|---|---|---|---|---|---|
| 5,665,122 | A | * | 9/1997 | Kambin | 623/17.16 |
| 5,836,948 | A | * | 11/1998 | Zucherman et al. | 606/249 |
| 6,582,433 | B2 | * | 6/2003 | Yun | 606/249 |
| 6,730,126 | B2 | * | 5/2004 | Boehm et al. | 623/17.15 |
| 7,695,513 | B2 | * | 4/2010 | Zucherman et al. | 623/17.11 |
| 7,749,252 | B2 | * | 7/2010 | Zucherman et al. | 606/248 |
| 2005/0010293 | A1 | * | 1/2005 | Zucherman et al. | 623/17.11 |
| 2005/0101955 | A1 | | 5/2005 | Zucherman et al. | |
| 2005/0261769 | A1 | * | 11/2005 | Moskowitz et al. | 623/17.11 |
| 2006/0241614 | A1 | * | 10/2006 | Bruneau et al. | 606/69 |
| 2006/0247640 | A1 | * | 11/2006 | Blackwell et al. | 606/71 |
| 2006/0247770 | A1 | * | 11/2006 | Peterman | 623/17.11 |
| 2006/0264939 | A1 | * | 11/2006 | Zucherman et al. | 606/61 |
| 2006/0293662 | A1 | | 12/2006 | Boyer et al. | |
| 2007/0151116 | A1 | * | 7/2007 | Malandain | 33/512 |
| 2007/0179500 | A1 | | 8/2007 | Chin et al. | |
| 2008/0114358 | A1 | | 5/2008 | Anderson et al. | |
| 2008/0161933 | A1 | * | 7/2008 | Grotz et al. | 623/17.16 |

(Continued)

FOREIGN PATENT DOCUMENTS

WO 2009036156 A1 3/2009

*Primary Examiner* — Ellen C Hammond
*Assistant Examiner* — Jacqueline Johanas
(74) *Attorney, Agent, or Firm* — Gifford, Krass, Sprinkle, Anderson & Citkowski, P.C.; Douglas J. McEvoy

(57) ABSTRACT

A support insert located between succeeding vertebrae and which includes a body having a specified shape and size and which is located in a space existing between succeeding process portions associated with the vertebrae. The body includes a generally boomerang shape in cross section with inner and outer ramped and displaceable pieces in order to seat against a surface of each vertebrae process. A collection of clips, anchors and/or frictional surface teeth are provided to assisting in locating and gripping opposing vertebral locations between which the body is applied.

6 Claims, 4 Drawing Sheets

(56) References Cited

U.S. PATENT DOCUMENTS

| | | |
|---|---|---|
| 2008/0167657 A1 | 7/2008 | Greenhalgh |
| 2010/0174316 A1* | 7/2010 | Zucherman et al. .......... 606/249 |
| 2010/0280550 A1* | 11/2010 | Reo et al. ...................... 606/249 |
| 2010/0292799 A1* | 11/2010 | Hansell et al. ............. 623/17.15 |
| 2012/0109205 A1* | 5/2012 | Mitchell et al. ................ 606/249 |
| 2014/0088713 A1* | 3/2014 | Greenhalgh et al. ....... 623/17.16 |

\* cited by examiner

ELEVATING INSERT FOR CERVICAL SPINAL VERTEBRAE

CROSS-REFERENCE TO RELATED APPLICATIONS

This Application claims the benefit of U.S. Provisional Application 61/184,183 filed on Jun. 4, 2009.

FIELD OF THE INVENTION

The present invention discloses an insert for providing inter cervical vertebrae C1-C7 support, such as in order to maintain positioning of the vertebrae and to prevent misalignment and/or pinching of the spinal nerve and its associated branches.

BACKGROUND OF THE INVENTION

The prior art is documented with various types of spinal immobilizing and spinal fusion devices. The most common of these is the provision of a titanium plate and screws for affixing the plate to any plurality of vertebrae, such as for the purpose of immobilizing the vertebrae to prevent pinching of the spinal nerve and associated branches. The shortcomings of such spinal fusion processes include the dramatically invasive nature of the implantation surgery, as well as the degree such implantation reduces flexibility and attendant quality of life for the individual, all in the interest of pain management.

SUMMARY OF THE INVENTION

The present invention discloses a support insert located between succeeding vertebrae and which includes a body having a specified shape and size which is located in a space existing between succeeding process portions associated with the vertebrae. The body includes a generally boomerang shape in cross section with inner and outer ramped and displaceable pieces in order to seat against a surface of each vertebrae process.

A collection of clips, anchors and/or frictional surface teeth are provided to assisting in locating and gripping opposing vertebral locations between which the body is applied. An outer piece can be constructed from a softer plastic, with an inner piece constructed of a harder plastic which is displaceable in an inward inserting fashion within an aperture defined in the outer piece in order to outwardly bulge and expand the outer piece to a desired spacing dimension. Additional features include the inner piece exhibiting a ramped configuration, the outer piece further including first and second portions which are laterally split along their sides and supported in controlled expandable fashion around said inner piece.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 7A:
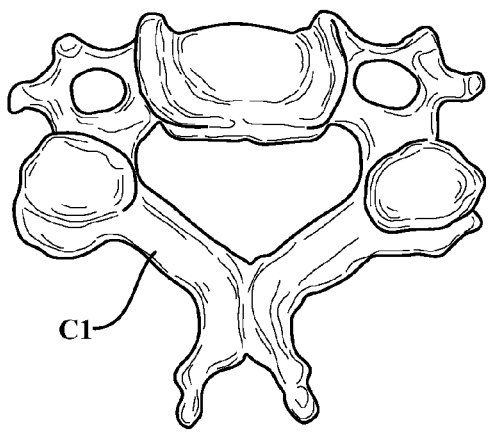
FIGS. 7A-7E are Prior Art illustrations setting forth, in succession, the C1, C2, C2 side, C3-C6 side and C7 cervical vertebrae to which the elevating insert of the present invention is applied.

Referring now to the several illustrations, the present invention discloses an insert for providing location specific and inter cervical vertebrae C1-C7 support, such as in order to maintain positioning of the vertebrae and to prevent misalignment and/or pinching of the spinal nerve and its associated branches. These in particular include the prior art illustrations of FIGS. 7A-7E setting forth, in succession, the C1 (FIG. 7A), C2 (FIG. 7B), C2 side (FIG. 7C), C3-C6 (FIG. 7D) side and C7 (FIG. 7E) cervical vertebrae to which the elevating insert of the present invention is applied.

Figure 7B:
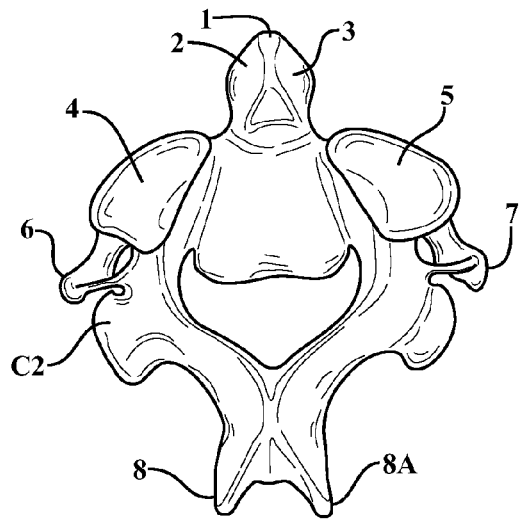
Figure 7C:
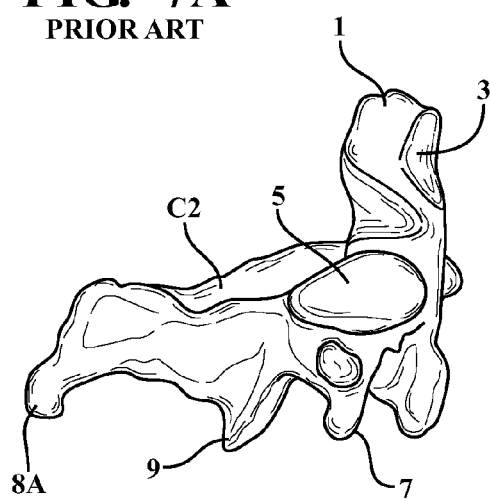
Figure 7D:
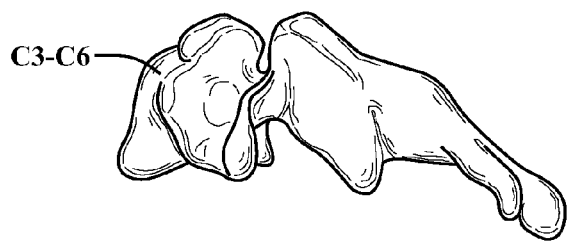
Figure 7E:
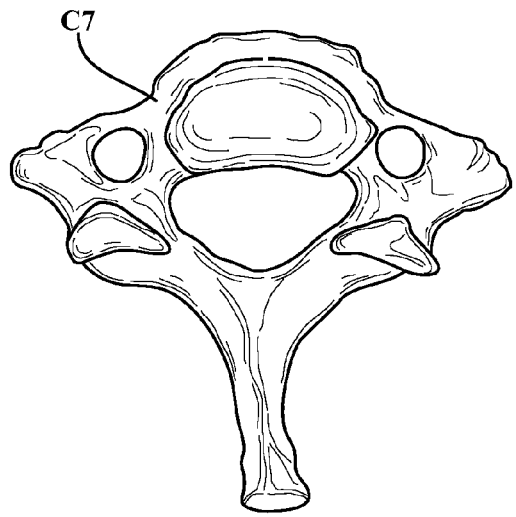

An exemplary description of the C2 vertebrae illustrated in front and side profile in FIGS. 7B and 7C, respectively illustrates a forward most dens 1 with alar ligaments 2 and 3, superior articular surfaces 4 and 5, transverse processes 6 and 7, spinous processes 8 and 8A and (underside) inferior articular process 9. The purpose of the following brief description is intended to be illustrative of the unique configurations associated with the cervical vertebrae, and with which the adjustable insert of the present invention is employed.

Referring again to the prior art illustrations of FIGS. 7A-7E identified at C1-C7, a general explanation of each of the cervical spinal vertebrae as commonly known is provided as follows. The C1 vertebrae, or atlas, is the topmost vertebra and, along with the C2 vertebrae, forms a joint connecting the skull and spine. Its chief peculiarity is that it has no body, and this is due to the fact that the body of the atlas has fused with that of the next vertebra.

The next succeeding C2 or axis vertebrae forms the pivot upon which C1 rotates. The most distinctive characteristic of this vertebral bone is the strong odontoid process (dens) which rises perpendicularly from the upper surface of the body. The body is deeper in front than behind, and prolonged downward anteriorly so as to overlap the upper and front part of the third vertebra.

The general characteristics of the succeeding third through sixth (C3-C6) cervical vertebrae include them being relatively small, as well as broader from side to side than from front to back. The anterior and posterior surfaces are flattened and of equal depth; the former is placed on a lower level than the latter, and its inferior border is prolonged downward, so as to overlap the upper and forepart of the vertebra below. Additionally, the upper surface is concave transversely, and presents a projecting lip on either side, whereas the lower surface is concave from front to back, convex from side to side, and presents laterally shallow concavities which receive the corresponding projecting lips of the underlying vertebra. The transverse processes are each pierced by the foramen transversarium, which, in the upper six vertebrae, gives passage to the vertebral artery and vein, as well as a plexus of sympathetic nerves. Each process consists of an anterior and a posterior part. Finally, the C7 vertebrae illustrated is notable in that it includes a long and prominent spinous process.

Figure 1:
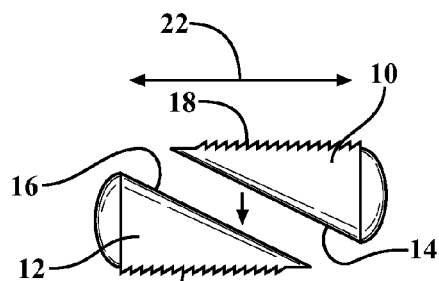
FIG. 1 is a plan cutaway view illustration of a two piece height adjustable insert exhibiting first and second ramp displaceable surfaces for use between succeeding cervical vertebrae and according to a first preferred embodiment of the present invention.

Referring now first to FIG. 1, a representative plan cutaway view illustration is shown in partially exploded fashion of the inner functioning components associated with the two piece height adjustable insert, including first piece 10 and second inter-engaging piece 12. Each of the insert pieces are illustrated in side disposed and generally flattened profile and which are constructed such as of a synthetic plastic or composite (such as with any of harder/softer plastic mixtures as well as admixtures with ceramics, metal or the like). The insert pieces 10 and 12 are illustrated as separated, however it is understood that they can be slidably connected in any desired channeled or grooved fashion, and in order to prevent inadvertent separation within the installed environment between the cervical spinal vertebrae.

As further shown, each of the pieces 10 and 12 exhibit smooth contacting ramp displaceable surfaces, see further at 14 and 16, for providing height adjustability when installed and displaced between succeeding cervical vertebrae. Opposite facing exterior surfaces are further shown at 18 and 20, respectively, and exhibit roughened portions, such as frictional engendering projections and serrations for anchoring the pieces 10 and 12 at desired locations within the inter-cervical spinal environment.

As will be additionally described in succeeding embodiments, the insert pieces 10 and 12 can also be undercut anchor secured at fixed locations to succeeding vertebrae. As further shown by bi-directional arrow 22, the respective pieces 10 and 12 are translated relative to one another in the direction of the ramped surfaces, and in order to establish a desired height defining displacement, at which point the individual pieces are either frictionally and/or anchor secured in place.

Figure 2:
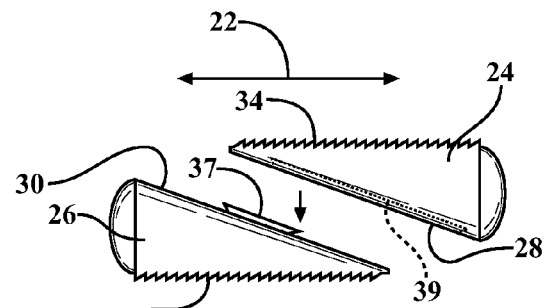
FIG. 2 is a similar illustration of a two piece height adjustable insert engageable between succeeding cervical vertebrae.

FIG. 2 is a similar partially exploded illustration of a two piece height adjustable spacer insert adapted to be engageable between succeeding cervical vertebrae and in which likewise generally dimensionally flattened first and second portions 24 and 26 are illustrated exhibit lengthened configurations, such as in comparison to that shown in FIG. 1. The lengthened spacer portions 24 and 26 correspond to different installation environments relating to opposing surfaces of succeeding cervical vertebrae (such as being resized for inter-vertebral support at opposing vertebrae locations having specific dimensions) and in order to provide a greater degree of adjustability.

Figure 3:
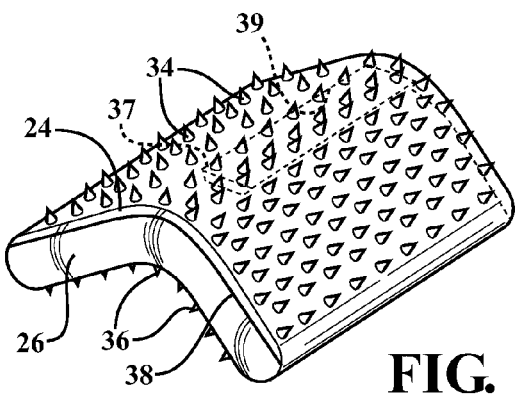
FIG. 3 is a perspective view of a two piece insert and exhibiting first and second substantially boomerang cross sectional shaped portions with inter-engaging ramped surfaces and further showing roughened and frictional engaging outer surfaces.

Referring now to FIG. 3, a perspective view is shown of an assembled two piece spacer, such as shown by inter-engaging and lengthwise displaceable pieces 24 and 26 in FIG. 2, and in which the plastic pieces collectively exhibit a specified length, width and thickness with a substantially boomerang cross sectional shape and further having inter-engaging ramped surfaces (see again as shown at 28 and 30 in FIG. 2 but hidden from view in the assembled fashion of FIG. 3), as well as further showing roughened and frictional engaging (e.g. teethed) outer surfaces 32 and 34. Separation line 38 in FIG. 3 defines the location of the mating ramped surfaces of the insert pieces 24 and 26 and further such that, upon sliding the pieces along their opposing ramped profiles, the overall height dimension of the spacer insert is modified to correspond to a desired environment located between succeeding spinal vertebrae.

Figure 3A:
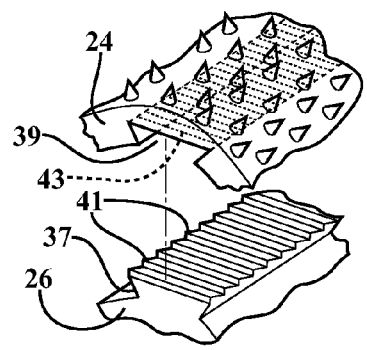
FIG. 3A is an inset view in exploded fashion of a serrated and uni-directional engagement established between flat adhering surfaces of the portions in FIG. 3.

Although not visible in FIG. 3, a linear seating tab and slot arrangement (see as depicted in side profile in FIG. 2 by one or more tabs 37 associated with component 26 which seat within a recess channel or slot 28, further shown in phantom in component 24) constitutes but one non-limiting example of a linearly displaceable engagement established between flattened contact surfaces of the insert pieces 24 and 26 and which enables the pieces to be linearly displaced and appropriately widened/narrowed as desired to fit according to a predetermined thickness profile. As further shown in the exploded inset view FIG. 3A, the tab 37 and slot 39 include inter-engaging serrated or ratcheting portions, and 41 and 43, respectively, which are adjustable in one direction so that the pieces 24 and 28 may be locked at a desired inter-displaced position according to a desired engaging and installation position (see as further shown in FIGS. 5A and 5B).

Figure 4A:
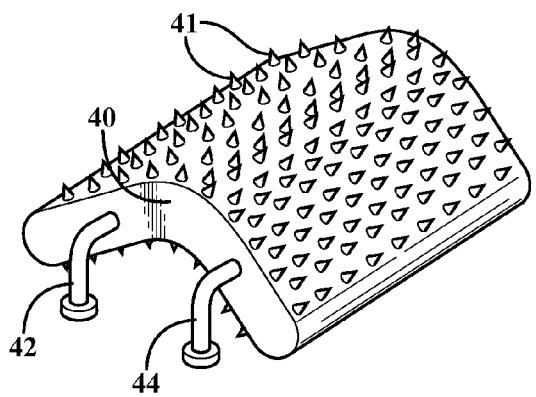
FIG. 4A is an illustration of a further configuration of holding insert according to another preferred embodiment and illustrating edge extending and angled locating clips for securing to such as an undercut defined location in a succeeding natural vertebrae.

FIG. 4A is an illustration of a further configuration of holding spacer insert, such as illustrating a single portion 40 according to another preferred embodiment, and further illustrating edge extending and angled locating clips 42 and 44 extending from an edge of the insert 40 for securing to such as an undercut defined location (not shown) which is formed by an appropriate drilling process in a succeeding natural vertebrae. The insert portion 40 can exhibit a similar boomerang shape in cross section, such as in order to be mounted or otherwise frictionally secured between such as the super or inferior process portions (such further again enabled by the provision of teethed projections or the like exhibited upon outer facing surfaces) or other suitably configured locations defined between the succeeding cervical vertebrae.

As further shown, the insert 40 can also include roughened projections or like surfaces 41 which assist in locating and fixing in a desired installation location associated with a vertebral location. The clip portions 42 and 44 terminate in outwardly and increased diameter portions, these corresponding with undercut defined locations formed in a succeeding vertebrae (such as which are further created through the assistance of a suitable undercut aperture defining drill bit associated with the machining process) and in order to anchor the insert 40 at a desired location between opposing vertebrae surfaces.

Figure 4B:
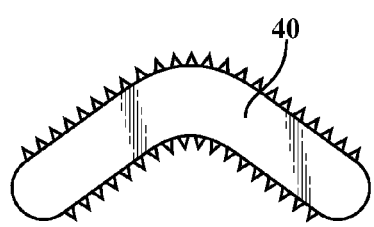
FIG. 4B is an end view illustration of the spacer insert shown in FIG. 4A.
Figure 4C:
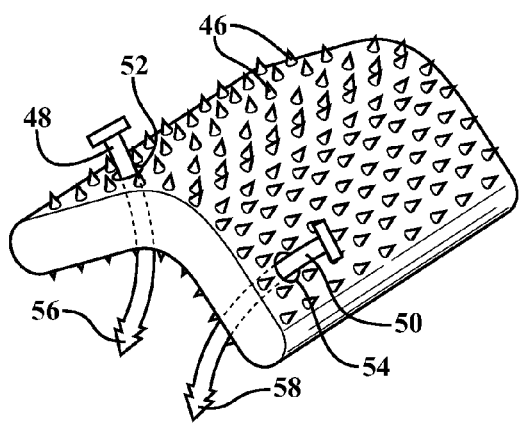
FIG. 4C is a perspective illustration of a spacer insert according to a still further preferred embodiment according to the present invention and illustrating the feature of first and second angularly displaceable anchors engageable through apertures in the insert and in order to anchor the insert to a succeeding vertebrae.

Referring to FIG. 4B, an end view illustration of the spacer insert 40 shown in FIG. 4A is again illustrated and indicates an average thickness dimension ranging, according to one non-liming variant, from 4 mm upwards, it being further understood that the size and shape of the inserts disclosed herein can be varied within the scope of the invention. FIG. 4C is a perspective illustration of a spacer insert 46 according to a still further preferred embodiment according to the present invention and illustrating the feature of first and second angularly displaceable anchors 48 and 50, these exhibiting elongated fasteners which are engageable through apertures 52 and 54 defined through the insert 46 and in order to anchor a previously positioned insert 46 to mating aligned and previously machined aperture defined in a succeeding vertebrae. Further shown are enlarged engaging ends 56 and 58 associated with the anchors 48 and 50, these optionally including reverse angled deflecting portions for resistance fitting within the aligning undercut recesses, such as in a press-fit fashion.

Figure 5A:
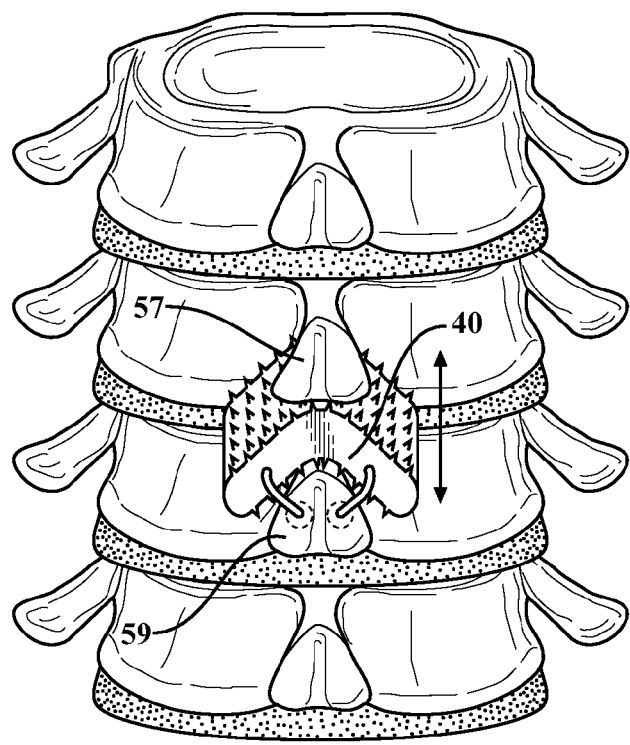
FIG. 5A is an environmental illustration showing the insert of FIG. 4A in engaged fashion between succeeding vertebrae.

FIG. 5A is an environmental illustration showing the one piece insert 40 of FIG. 4A in engaged fashion between succeeding vertebrae, such as articular process portions 57 and 59 extending rearwardly from succeeding cervical spinal bodies. As previously described, the human spinal column includes cervical vertebrae C1-C7, with which the height adjusting inserts are particularly suited for establishing a desired spacing between any of the spinous process, superior articular process, inferior articular process, anterior tubercle of transverse process, and posterior tubercle of transverse process.

Figure 5B:
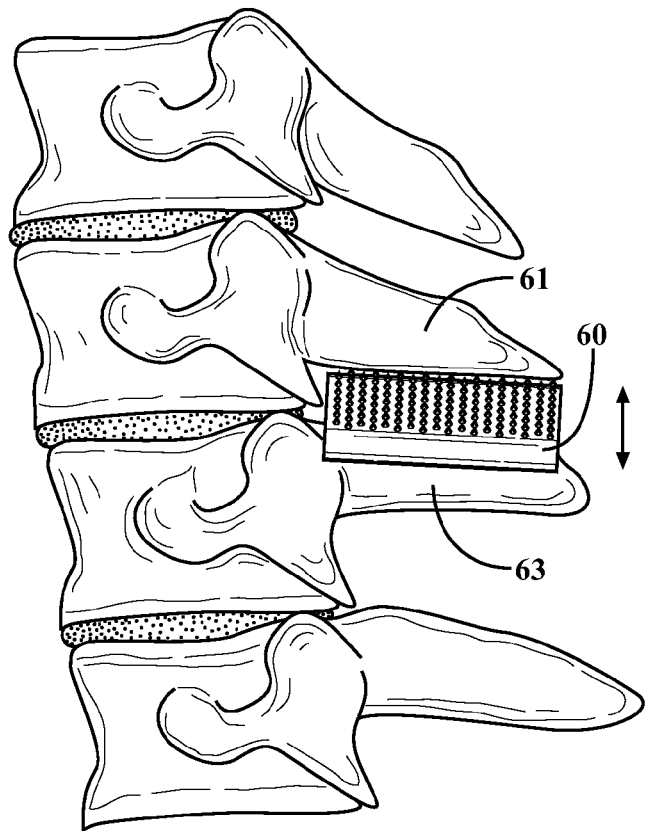
FIG. 5B is a rotated environmental view showing and further arrangement of spacer insert engaged between such as an elongated process component of an existing spinal vertebrae.

Referring now to FIG. 5B, a rotated environmental view is further shown and in which a further arrangement of spacer clip 60, similar to the two piece and height adjustable clip in FIG. 3, is engaged between such as an elongated process components 61 and 63 of existing cervical spinal vertebrae, these corresponding to any of the spinous processes described in reference to the prior art illustrations C1-C7 described herein.

Figure 6A:
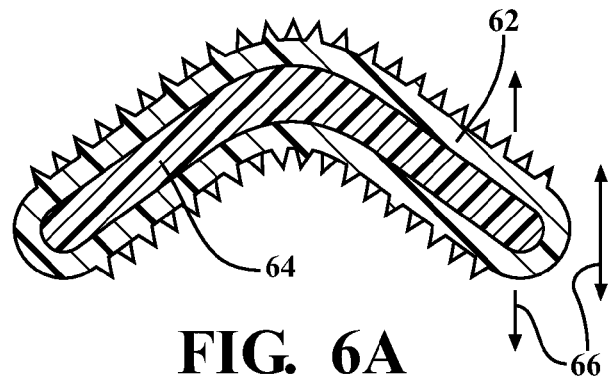
FIG. 6A is an end view illustration of a height adjustable spacer insert according to a further preferred embodiment of the present invention and illustrating an outer piece constructed from such as a soft plastic, as well as an inner piece constructed of a second harder plastic and which is displaceable in an inward inserting fashion in order to outwardly bulge and expand the outer piece to a desired spacing dimension.

Finally, FIG. 6A is an end view illustration of a height adjustable spacer insert according to a further preferred embodiment of the present invention and illustrating an outer piece 62 constructed from such as a soft plastic, as well as an inner piece 64 constructed of a second harder plastic with a ramped profile and which is displaceable in an inward inserting fashion in order to outwardly bulge and expand (see arrows 66) of the outer piece to a desired spacing dimension. Similar to previous embodiments described, the mating pieces 62 and 64 each can exhibit a generally boomerang shape profile in cross section, with the softer outer piece 62 exhibiting a central recessed and likewise boomerang shaped pocket within which the inner harder piece 64 seats and which, upon displacing the ramp profiled inner piece 62, causes the softer outer piece 62 to bulge outwardly.

Figure 6B:
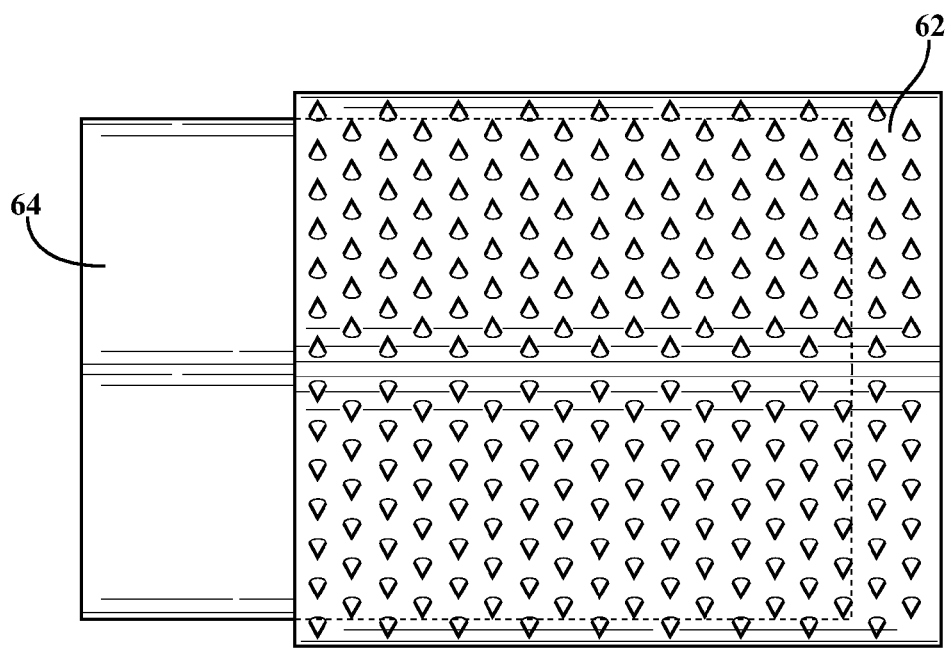
FIG. 6B is a top view of the spacer insert shown in FIG. 6A.
Figure 6C:
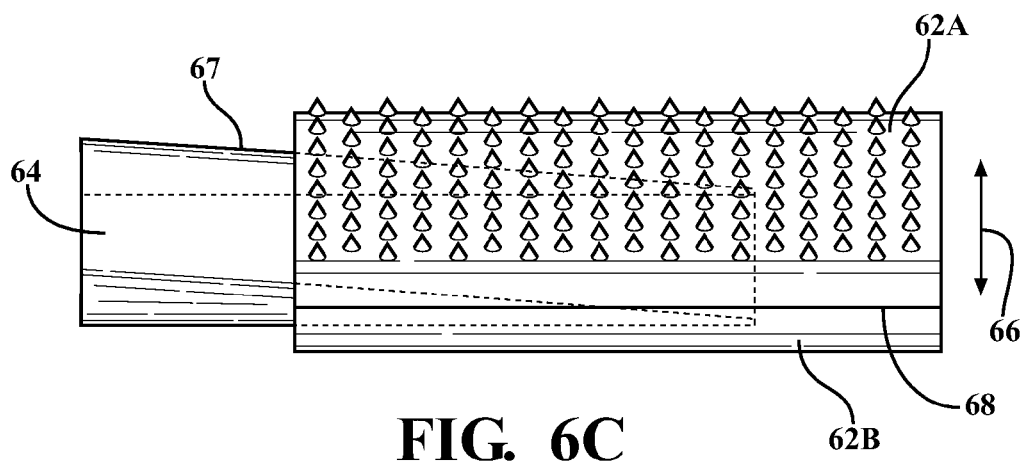
FIG. 6C is a side view of the insert of FIG. 6A and illustrating the ramped configuration of the inner displaceable piece for outwardly displacing the outer piece(s)

FIGS. 6B and 6C are top and side views of the spacer insert arrangement further illustrating the ramped configuration of the inner displaceable piece 64, such as shown by tapered surface 67 of harder inner piece 64 in FIG. 6C, and which upon displacement results in outwardly displacing the outer piece 62 in the direction of arrow 66. The outer piece 62 can also be provided as first and second pieces which are laterally split along their sides (see at 68 in FIG. 6C) which are supported in some controlled expandable fashion around the inner displaceable piece 64. This can further contemplate (in one non-limiting embodiment) further elastomeric side located portions (not shown) which interconnect the upper 62A and lower 62B split halves associated with the outer deformable piece in FIG. 6C, and which respond to the inserting inner piece 64 by separating along the boundary 68.

Having described my invention, other and additional preferred embodiments will become apparent to those skilled in the art to which it pertains and without deviating from the scope of the appended claims.

I claim:

1. A height adjustable spacer insert configured to be supported between elongated processes associated with first and second succeeding spinal vertebrae, said insert comprising:
   an outer piece having a boomerang shaped cross sectional profile exhibited by first and second angled sides and an interconnecting midpoint, said outer piece is constructed of a softer material, a boomerang shaped inner perimeter surface extending from an edge of said outer piece and inwardly to define a pocket within said outer piece;
   anchors extending from said outer piece and adapted to engage a selected one of the elongated processes for mounting said outer piece so that said midpoint is adapted to being supported upon the elongated process in a seated fashion and said pocket faces away from a main disk associated with the vertebra;
   an inner piece constructed of a harder material and having a boomerang shape cross sectional profile, an exterior of said inner piece being ramped along a length extending dimension between a first end having a smaller boomerang shaped dimension and a second end having a larger boomerang shaped dimension; and
   said first end of said inner piece being received within a receiving end of said pocket, wherein continued inward displacement of said inner piece causes uniform expansion of said softer outer piece along its cross sectional dimension and into supporting contact with an underside of the other elongated process.

2. The insert as described in claim 1, further comprising pluralities of friction promoting teeth disposed on each of opposite facing and process engaging surfaces of said outer piece to maintain a spatial position between the vertebrae.

3. The insert as described in claim 1, said anchors further comprising clip portions integrally extending from edge locations of said outer piece, said clip portions each having an angled shape with enlarged ends adapted to engage with the selected elongated process.

4. The insert as described in claim 1, said anchors each further comprising an elongate body displacing through apertures defined through said outer piece.

5. The insert as described in claim 4, said elongate bodies each further comprising an enlarged head at one end which, upon being fully inserted, engages upper surface locations of said outer piece, opposite process engaging ends of said elongate bodies exhibiting a reverse angled profile.

6. The insert as described in claim 1, further comprising opposite side locations of said outer piece which are laterally split during expansion by said inner piece.

* * * * *